US00PP15991P2

(12) United States Plant Patent
Olesen et al.

(10) Patent No.: US PP15,991 P2
(45) Date of Patent: Sep. 20, 2005

(54) ***CLEMATIS* PLANT NAMED 'EVIPO030'**

(50) Latin Name: *Clematis viticella*
Varietal Denomination: Evipo030

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 43 days.

(21) Appl. No.: 10/838,419

(22) Filed: May 4, 2004

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation in glasshouses with a very compact growth habit and profuse violet flowers. The variety successfully propagates from softwood cuttings and is suitable for cultivation in commercial glasshouses. This new and distinct variety has shown to be uniform and stable in the resulting generations from asexual propagation.

2 Drawing Sheets

Botanical classification: Genus—*Clematis*. Species—*viticella*.

Variety denomination: 'Evipo030'.

Commercial classification: Early large flowered cultivar.

SUMMARY OF THE INVENTION

The present invention constitutes a new and distinct variety of *Clematis* which originated from a controlled crossing between the female parent, 'Silver Moon' (unpatented), and the male parent, an un-named, unpatented seedling.

The new *Clematis* may be distinguished from its female seed parent, 'Silver Moon', by the following combination of characteristics:

1. In one growing season, 'Evipo030' normally grows to less than 60 cm in height. The seed parent typically attains 2 meters height.
2. 'Evipo030' displays flowers with a diameter of 70–90 mm, while flowers of the seed parent are typically 130 mm.

The new *Clematis* may be distinguished from its male pollen parent, an un-named seedling, by the following combination of characteristics:

1. 'Evipo030' has a violet flower color. The pollen parent tends to be dark red-purple.
2. 'Evipo030' is more compact, attaining less than 60 cm in height in one growing season. The pollen parent attains more than 100 cm of height in one season's growth.

The two parents were crossed in 1995 and the resulting seed was planted in a controlled environment. The new variety is named 'Evipo030'.

The objective of the hybridization and selection of this *Clematis* variety for commercial glasshouse and nursery culture was to create a new and distinct variety with the unique qualities that this variety has:

1. Compact growth habit;
2. Violet flowers;
3. Suitable for commercial pot-plant culture without requiring a growing support structure.

These qualities required improvement in *Clematis* varieties that were in commercial cultivation and the objectives have been substantially achieved in the new variety, as evidenced by the unique combination of characteristics that are present in 'Evipo030' which distinguish it from all other varieties of which we are aware.

The seeds from the aforementioned hybridization were germinated and evaluations of the resulting seedling plants were conducted in a controlled environment. As a result, 'Evipo030' was selected by Raymond J. Evison and Mogens N. Olesen in their *Clematis* development program in Domarie Vineries Les Sauvagees, St. Sampsons, Guernsey, Channel Islands, United Kingdom in April 1996.

Asexual reproduction of 'Evipo030' by cuttings was first done by Raymond J. Evison and Mogens N. Olesen in Domarie Vineries Les Sauvagees, St. Sampsons, Guernsey, Channel Islands, United Kingdom in May 1996. This initial and subsequent asexual propagations have demonstrated that the characteristics of 'Evipo030' are true to type and are transmitted from one generation to the next.

BRIEF DESCRIPTION OF THE DRAWING

The accompanying color illustrations show as true as is reasonably possible to obtain in color photographs of this type:

FIG. 1.1 Bloom, upper side and lower side;

FIG. 1.2 Stem, leaves, bud at ¼ opening, closed flower bud;

FIG. 1.3 Stem and leaves;

FIG. 1.4 Stem and juvenile foliage.

FIG. 2.0 Flowers, flower buds, and leaves.

DETAILED DESCRIPTION OF THE VARIETY

The following is a detailed description of 'Evipo030', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Evithree', a patented variety described and illustrated in U.S. Plant Pat. No. 9,362 issued Nov. 7, 1995, is compared to 'Evipo030'. Chart 1 details several physical characteristics of 'Evipo030' and 'Evithree'.

CHART 1

| | 'Evipo030' | 'Evithree' |
|---|---|---|
| Flower Diameter | 70–90 mm | 40 to 50 mm |
| Growth height in one season | Less than 60 cm | 2.5 meters |
| Tepal upper surface | Violet N88C | Violet 88A |

FLOWER AND FLOWER BUD

Blooming habit:
- *Flowering period.*—Early spring, typically from April to May. Flowering recurs agin in autumn, typically during the months of August, September, and October.

Flower bud:
- *Size.*—25 to 35 mm in length. Bud diameter is 13 mm on average.
- *Bud form.*—Ovoid.
- *Bud color.*—Green Group 138B at ¼ opening.

Peduncle:
- *Surface.*—Smooth.
- *Length.*—30 mm average length.
- *Color.*—Red-Purple Group 60A.
- *Strength.*—Strong.

Receptacle: None.

Flower arrangement:
- *Location on vine.*—Flowers emerge from old, previous season's, and new, current season's growth.
- *Borne.*—Occasionally singly but also in clusters of 3–5 flowers arranged in compound cymes.

Flower bloom:
- *Size.*—70 to 90 mm in diameter. 15 mm in depth. Flower depth is largely the result of the protruding reproductive flower parts.
- *Profile.*—Upon opening, flowers are slightly concave. After opening flowers are flat with straight tepals.
- *Tepal color.*—Upon opening: Upper surface is Violet Group N88B. After opening: Upper surface is Violet Group N88C.
- *Variations.*—Lower surface about Violet Group N88C and can exhibit light green central bar along each tepal length, the color of Greyed Green Group 190B.
- *Fragrance.*—Very light floral scent.
- *Lastingness on plant.*—10–15 days.
- *Lastingness* (*cut flower*).—3–4 days.

Tepals:
- *Quantity.*—Average range is 6 to 8 tepals.
- *Size.*—40 mm in length by 25 mm wide.
- *Shape.*—Individual tepal shape is elliptic.
- *Cross section.*—Flat.
- *Margins.*—Entire.
- *Undulation of margin.*—Slight. Undulations occur 2 to 3 times along the margin.
- *Tepal apex.*—Narrowly acute.
- *Recurvature of tip.*—None.
- *Persistence.*—Normally tepals drop off cleanly after flowers have fully matured.
- *Arrangement.*—Tepals are arranged regularly.

Reproductive organs:
- *Arrangement.*—Open.
- *Pollen.*—Quantity: Average. Color: White Group 155 A.
- *Anthers.*—Size: 10 mm in length. Color: Red-Purple Group 59B. Quantity: 80–90 (actual count).
- *Filaments.*—Color: Greyed Green Group 192C. Length: 12–15 mm.
- *Pistils.*—Quantity: 70 to 80 (actual count).
- *Stigmas.*—10 mm in length. As flowers age, stigmas protrude further than the anthers.
- *Styles.*—Color: Greyed Green Group 192C. Length: 15 mm.

Seed characteristics:
- *Size.*—Individual seeds are 30 to 40 mm in length. The elongate plumule accounts for the majority of the length. 4 to 5 mm in diameter at at the base of the seed.
- *Shape.*—Circular to tear shaped with elongated plumule.

PLANT

Plant form: Climbing and bushy.

Plant growth: Very compact. Seasons growth to less than 60 cm in height. Average apread is 50 cm.

Hardiness: Trials to date demonstrate that the variety is hardy to USDA Cold Hardiness Zone 4.

Stems:
- *Color.*—Young wood: Green Group 137C, turning Red-Purple Group 59A. Older wood: Greyed-Orange Group 165C.
- *Internodes.*—Shape: Cylindrical. Length: 10 to 30 mm.
- *Surface.*—Young wood: Smooth. Older wood: Smooth.

Plant foliage:
- *Leaf characteristics.*—Deciduous.
- *Mature leaf form.*—Trifoliate. 3 leaves in pinnate form.
- *Compound leaf size.*—80 mm (l)×80 mm (w).
- *Abundance.*—There are 6 leaves per 10 cm of stem on average.
- *Color.*—Mature leaves: Upper surfaces are Green Group 137A. Lower surfaces are Green Group 137C. Juvenile leaves: Upper surfaces are Green Group 143A. Lower surfaces are Green Group 143C.

Plant leaves and leaflets:
- *Stipules.*—Absent.
- *Petioles.*—Size: Average length: 10 to 30 mm. Color: Red-Purple Group 59A. Clasping: By leaf petiole.
- *Petioloule.*—Length: 30 to 40 mm. Color: Green Group 137B occasionally Red-Purple Group 59A.
- *Leaf edge.*—Terminal leaflet margin is entire.
- *Leaflet shape.*—Generally ovate. Base is rounded. Leaflet apex is apiculate.
- *Margin.*—Entire.
- *Leaflet size.*—50 mm in length by 25 mm wide.
- *Surface texture.*—Upper surface is smooth. Lower surface is somewhat pubescent.
- *Thickness.*—Moderate.
- *Glossiness.*—Upper and lower side both glossy.

Disease resistance: Subject to any disease that normally attacks the species. However, the variety is more tolerant to mildew than other *Clematis* of which we are aware.

It is claimed:

1. A new and distinct variety of *Clematis* plant named 'Evipo030' as illustrated and described herein, due to its abundant violet flowers with good keepability, attractive long lasting foliage and exceptionally compact growth, year round flowering under glasshouse conditions, suitability for production from softwood cuttings in pots, durable flowers and foliage which make the variety suitable for distribution in the floral industry.

* * * * *

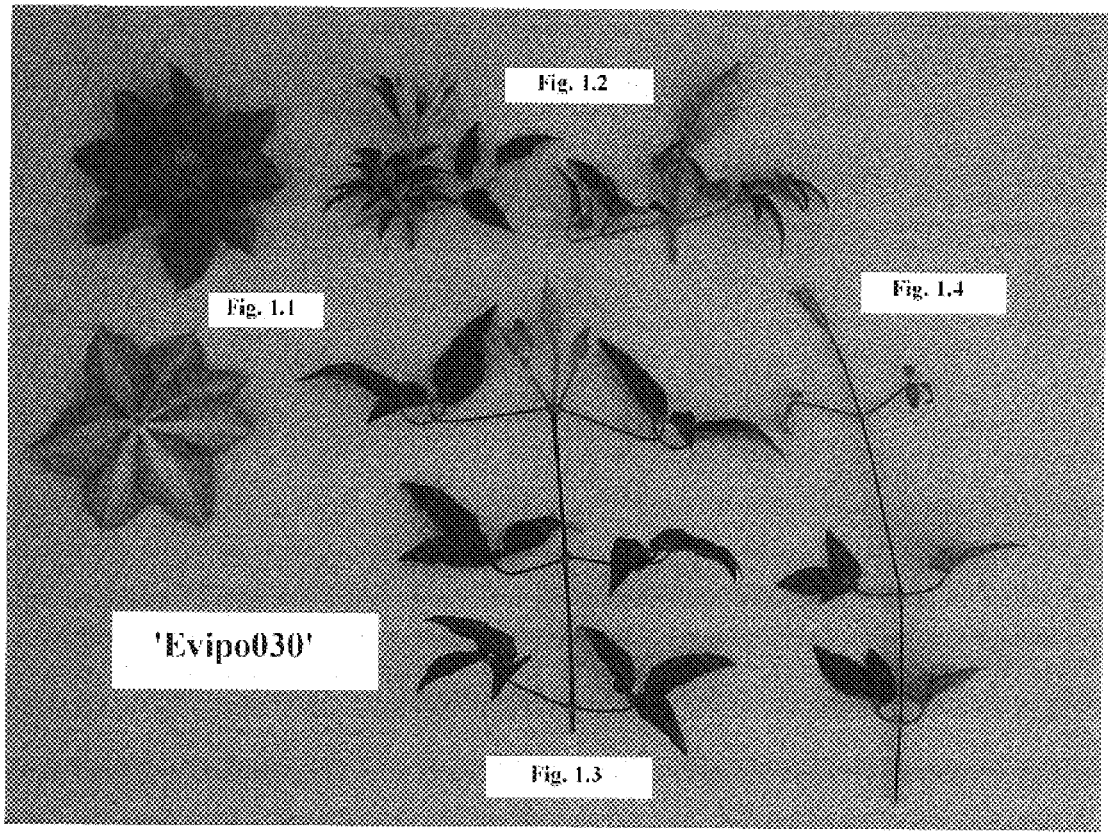
Fig. 1.2
Fig. 1.1
Fig. 1.4
'Evipo030'
Fig. 1.3

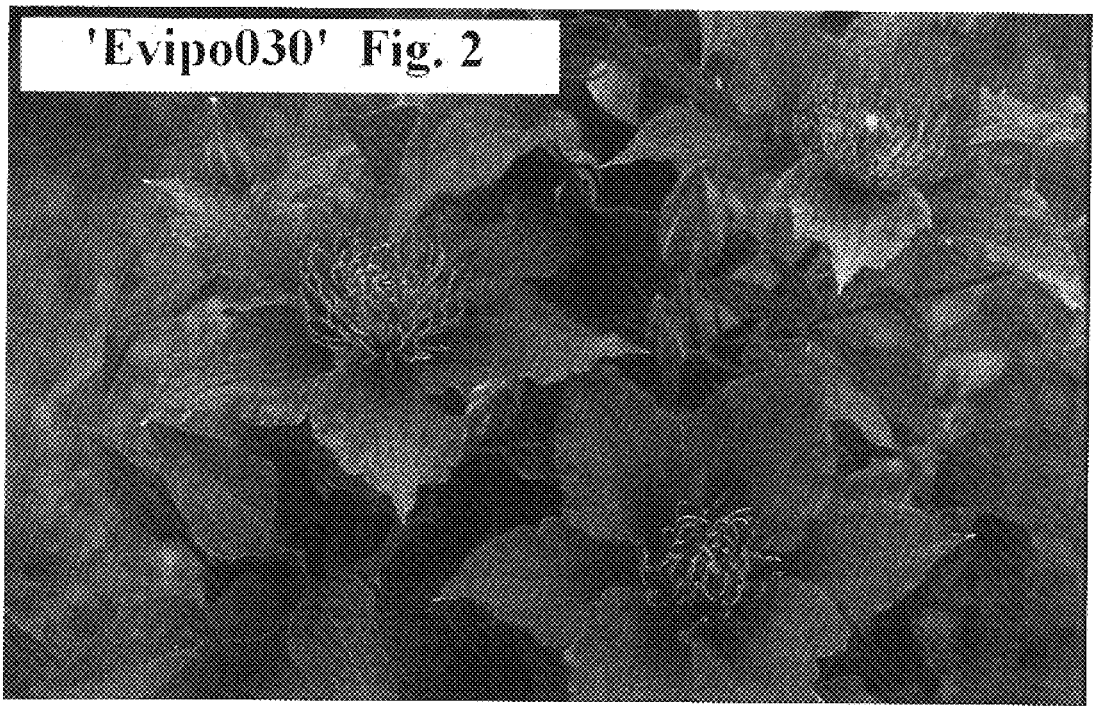
'Evipo030' Fig. 2